(12) United States Patent
Gannon et al.

(10) Patent No.: US 11,819,313 B2
(45) Date of Patent: Nov. 21, 2023

(54) SYSTEM AND METHOD OF USING BODY TEMPERATURE LOGGING PATCH

(71) Applicant: Blue Spark Technologies, Inc., Westlake, OH (US)

(72) Inventors: John Gannon, Shaker Heights, OH (US); Matt Ream, Naperville, IL (US); Frank Feddrix, Westlake, OH (US); Ruth Phillips, Collegeville, OH (US); Adam Perer, Pittsburgh, PA (US); Sashi Kolli, Virginia Beach, VA (US)

(73) Assignee: BLUE SPARK INNOVATIONS, LLC, Westlake, OH (US)

( * ) Notice: Subject to any disclaimer, the term of this patent is extended or adjusted under 35 U.S.C. 154(b) by 325 days.

(21) Appl. No.: 17/064,708

(22) Filed: Oct. 7, 2020

(65) Prior Publication Data

US 2021/0100454 A1 Apr. 8, 2021

Related U.S. Application Data

(60) Provisional application No. 62/934,188, filed on Nov. 12, 2019, provisional application No. 62/911,850, filed on Oct. 7, 2019.

(51) Int. Cl.
*A61B 5/01* (2006.01)
*A61B 5/00* (2006.01)
*G06N 3/08* (2023.01)

(52) U.S. Cl.
CPC .............. *A61B 5/01* (2013.01); *A61B 5/0008* (2013.01); *A61B 5/7275* (2013.01); *A61B 5/746* (2013.01); *G06N 3/08* (2013.01)

(58) Field of Classification Search
None
See application file for complete search history.

(56) References Cited

U.S. PATENT DOCUMENTS 9,183,738 B1 11/2015 Allen, Sr.
2005/0245839 A1 11/2005 Stivoric et al.
(Continued)

FOREIGN PATENT DOCUMENTS

KR 10-2018-0099434 A 9/2018

OTHER PUBLICATIONS

Titov, Aleksei et al. "The biological basis and clinical symptoms of CAR-T therapy-associated toxicites." Cell death & disease vol. 9,9 897. Sep. 4, 2018, doi:10.1038/s41419-018-0918-x (Year: 2018).*
(Continued)

*Primary Examiner* — Benjamin S Melhus
(74) *Attorney, Agent, or Firm* — Pearne & Gordon LLP

(57) ABSTRACT

Continuous temperature monitors can be used to collect frequent temperature data over large periods of time. A machine learning system trained with collected temperature data can be used to predict future temperature data for patients. Such predictions can be clinically beneficial for disease states in which fever can be fatal, particularly for those fevers having fast onset. For example, patients undergoing chimeric antigen receptor T-cell (CAR-T) therapy may suffer fevers caused by cytokine release syndrome (CRS). Accordingly, a continuous temperature monitor is used to collect temperature data from CAR-T patients with high risk of CRS (or like patients with high fever risk), and the collected temperature data processed by a machine learning system to predict the patient's future temperature profiles. Results of analysis of the predicted temperature profiles may then be provided to the patient and/or clinician.

18 Claims, 9 Drawing Sheets

(56) References Cited

U.S. PATENT DOCUMENTS

| | | | | |
|---|---|---|---|---|
| 2006/0161074 | A1* | 7/2006 | Liao | G01K 13/20 |
| | | | | 374/E1.004 |
| 2009/0175317 | A1* | 7/2009 | Chan | G01J 5/02 |
| | | | | 374/170 |
| 2011/0213559 | A1* | 9/2011 | Pollack | A61B 5/7221 |
| | | | | 702/19 |
| 2012/0319847 | A1* | 12/2012 | Heller | G01K 13/20 |
| | | | | 600/549 |
| 2013/0137940 | A1* | 5/2013 | Schafer | A61B 10/0012 |
| | | | | 600/301 |
| 2014/0088443 | A1* | 3/2014 | Van Den Heuvel | |
| | | | | A61B 5/6824 |
| | | | | 600/483 |
| 2014/0149065 | A1* | 5/2014 | Pompei | G16H 50/20 |
| | | | | 702/131 |
| 2014/0378863 | A1* | 12/2014 | Schafer | G16H 40/63 |
| | | | | 600/551 |
| 2015/0297146 | A1* | 10/2015 | Pollack | A61B 5/7221 |
| | | | | 702/19 |
| 2016/0302671 | A1* | 10/2016 | Shariff | A61B 5/7246 |
| 2017/0024536 | A1 | 1/2017 | Webb et al. | |
| 2017/0030781 | A1* | 2/2017 | Pompei | G16H 50/20 |
| 2018/0247714 | A1 | 8/2018 | Lee | |
| 2018/0249947 | A1* | 9/2018 | Seegmiller Maudlin | |
| | | | | A61B 5/0816 |
| 2019/0046033 | A1* | 2/2019 | Gannon | G01K 1/024 |
| 2019/0192010 | A1* | 6/2019 | Mane | A61B 5/165 |
| 2019/0216333 | A1* | 7/2019 | Lai | A61B 5/0064 |
| 2020/0011746 | A1* | 1/2020 | Allen, Sr. | A61B 5/01 |
| 2020/0288983 | A1* | 9/2020 | Telfort | A61B 5/01 |

OTHER PUBLICATIONS

International Preliminary Report on Patentability for corresponding International Application No. PCT/US2020/054476 dated Apr. 12, 2022.

International Search Report for corresponding International Application No. PCT/US2020/054476 dated Jan. 29, 2021.

Written Opinion for corresponding International Application No. PCT/US2020/054476 dated Jan. 29, 2021.

Dakappa, Pradeepa H. et a., "A Predictive Model to Classify Undifferentiated Fever Cases Based on Twenty-Four-Hour Continuous Tympanic Temperature Recording", Journal of Healthcare Engineering, 2017, vol. 2017, Article ID 5707162, pp. 1-6.

Mathur, Neha et al., "Skin Temperature Prediction in Lower Limb Prosthese", IEEE Journal of Biomedical and Health Informatics, 2016, vol. 20, No. 1, pp. 158-165.

Al-Barade, Magde & Alekberli, Tural & van Heerden, Peter. (2020). Continuous Non-Invasive Temperature Monitoring as a Means of Early Detection of Sepsis. Intensive Care Medicine Experimental. 8. 345-346. 10.1186/s40635-020-00354-8 Abstract and Poster.

Australian Examination Report dated Feb. 15, 2023 for corresponding Australian Application No. 2020362178.

Extended European Search Report dated Mar. 31, 2023 for corresponding European Application No. 20873904.5.

\* cited by examiner

SYSTEM AND METHOD OF USING BODY TEMPERATURE LOGGING PATCH

CROSS-REFERENCE TO RELATED APPLICATIONS

This application claims priority to U.S. Provisional Application No. 62/911,850, filed on Oct. 7, 2019, and titled "SYSTEM AND METHOD OF USING BODY TEMPERATURE LOGGING PATCH," and to U.S. Provisional Application No. 62/934,188, filed on Nov. 12, 2019, and titled "SYSTEM AND METHOD OF USING BODY TEMPERATURE LOGGING PATCH," the entireties of which are herein incorporated by reference.

BACKGROUND

Recent cancer treatments have included various immunotherapies. Among these, chimeric antigen receptor T-cell (CAR-T) therapy involves engineering autologous T-cells harvested from a patient to express the chimeric antigen receptor (CAR) gene. The CAR gene elicits growth of a receptor on the T-cell that binds to special proteins on the surface of a patient's cancer cells. The harvested and then engineered cells are grown in vitro and then infused back into the patient. Once in the patient, the cells further continue to grow logarithmically and attack the patient's cancer cells, which are targeted by the CAR receptor.

CAR-T therapy has proven to be particularly successful in treating liquid tumors (e.g., hematological cancers such as leukemia and lymphomas). Similar T-cell immunotherapies include T-cell receptor (TCR) therapy where the T-cell is genetically engineered to produce a TCR protein that targets antigens inside of the cancer cells; and tumor-infiltrating lymphocyte (TIL) therapy where the harvested T-cells are from a solid tumor biopsy and thus already recognize the cancer cells.

In these therapies, however, the elevated number of T-cells causes an increase in cytokine levels in the patient. Such a cytokine increase can result in cytokine release syndrome (CRS), which is a common toxicity in patients receiving those therapies. CRS is characterized initially by a fever, which can escalate and progress quickly to life-threatening vasodilatory shock, capillary leak, hypoxia, and end-organ dysfunction. Table 1, below, illustrates the grades of CRS.

TABLE 1

| Recognized CRS grading criteria | | | | |
|---|---|---|---|---|
| CRS Parameter | Grade 1 | Grade 2 | Grade 3 | Grade 4 |
| Fever with | ≥38° C. | ≥38° C. | ≥38° C. | ≥38° C. |
| Hypotension | None | Not requiring vasopressors | One vasopressor with or without vasopressin | Multiple vasopressors (excluding vasopressin) |
| and/or | | | | |
| Hypoxia | None | Low-flow nasal canula or blow-by | High-flow nasal cannula, facemask, non-breather mask, or Venturi mask | Positive pressure (e.g., CPAP, BiPAP, intubation and mechanical ventilation) |

In view of the above, CAR-T therapies are required to employ a CRS mitigation strategy.

SUMMARY OF THE INVENTION

According to a first example of the present disclosure, a method comprises: receiving temperature data from a continuous temperature monitor, the temperature data being collected from a patient during a collection time period; inputting the received temperature data to a machine learning system, the machine learning system being trained to output prediction temperature data for a future time period; analyzing the prediction temperature data for indication of a fever; and transmitting a notification of a result of the analysis to a personal device of the patient and/or to a clinician.

In various embodiments of the above example, the machine learning system is remotely connected to the continuous temperature monitor and to the clinician via a network; the patient is undergoing or has undergone chimeric antigen receptor T-cell (CAR-T) therapy, and the fever is caused by cytokine release syndrome; the machine learning system is trained with temperature data collected from a patient during a cytokine release syndrome fever; the method further comprises correcting temperature data points having a value below a predetermined threshold prior to inputting the received temperature data to the machine learning system; analyzing the prediction temperature data for a fever comprises comparing values of the prediction temperature data to a predetermined threshold; analyzing the prediction temperature data for a fever comprises comparing a characteristic of the prediction temperature data to a predetermined threshold, the characteristics comprising: a rate of increase of the prediction temperature data, or a period of time the prediction temperature data is greater than a predetermined threshold; the collection time period is three hours and the future time period is one hour; the notification comprises a time series graph of the prediction temperature data; the notification comprises an alert and an instruction to the patient to seek medical attention when the result of the analysis indicates the fever; the machine learning system comprises a multi-step multi-layer perceptron network; the machine learning system comprises a univariate multi-step convolutional neural network; the machine learning system comprises a long-short-term memory model; the machine learning system comprises a sequence to sequence model; the notification is transmitted in substantially real time with the receipt of the temperature data.

DETAILED DESCRIPTION

Figure 1:
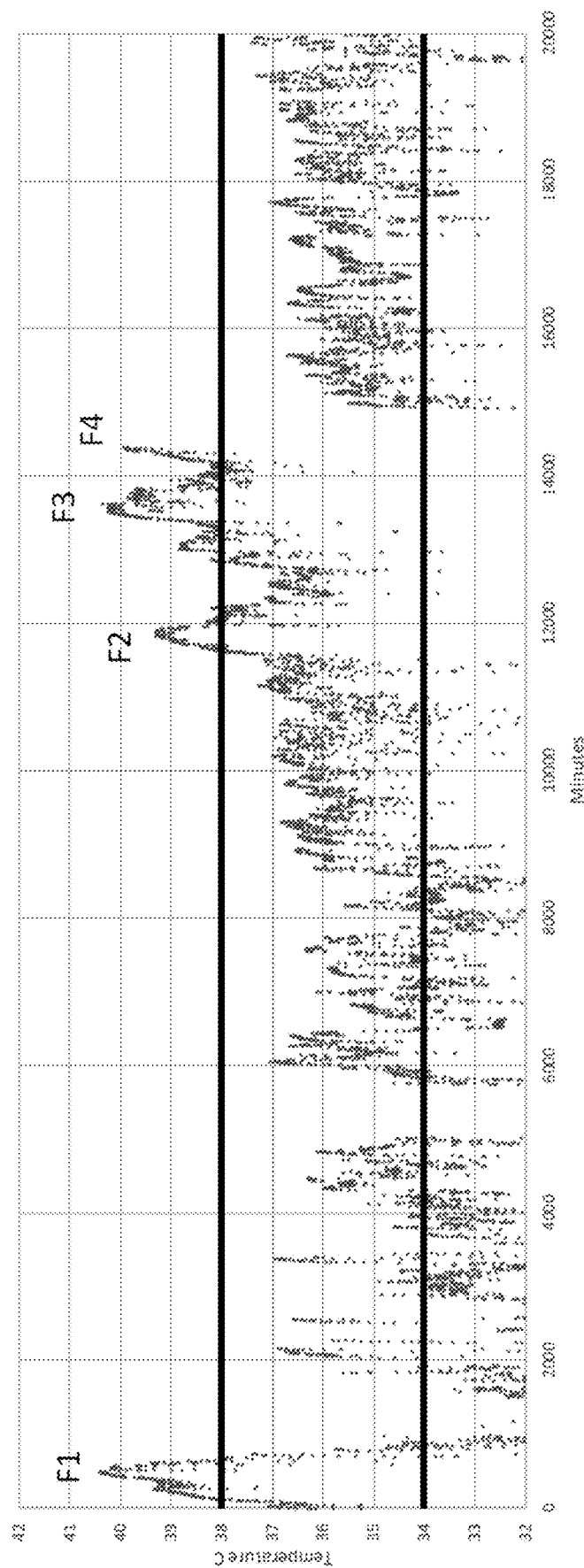
FIG. 1 illustrates an example CRS temperature profile from a first CAR-T patient.

Considering the above, CRS is treatable when in its initial stages but can become fatal particularly when progressed to Grade 4. As seen in Table 1, CRS is initially characterized by a fever. Therefore, early detection of fever in patients susceptible to CRS can help identify CRS onset so that it may be timely treated. Conventionally, the current standard of care for temperature monitoring is to record a patient's temperature every four hours, or approximately six times per day (i.e., per 24-hour period). However, such a relatively low-frequency temperature check is likely to miss early indications of CRS onset.

According to one embodiment of the present disclosure, early detection of a CRS fever may be accomplished via continuous temperature monitoring. Such continuous temperature monitoring may be realized, for example, with the body temperature logging patch described in U.S. patent application Ser. No. 13/926,508 filed on Jun. 25, 2013, now issued as U.S. Pat. No. 9,782,082; in U.S. patent application Ser. No. 14/587,626 filed on Dec. 31, 2014, now issued as U.S. Pat. No. 9,693,689; and in U.S. patent application Ser. No. 15/989,674 filed on May 25, 2018, now published as U.S. 2019/0046033, all of which are incorporated herein by reference.

The use of continuous temperature monitoring provides much higher frequency collection of patient temperatures. In several non-limiting examples, the above-described body temperature logging patch can record a patient's temperature at a frequency of once every ten seconds, or approximately 8,640 times per day (i.e., per 24-hour period). Various other frequency rates are considered, such as once every thirty seconds (i.e., 2,880 times per day), once every minute (i.e., 1,440 times per day), or once every five minutes (i.e., 288 times per day). Other frequencies of temperature data collection are also contemplated. As can be readily seen, automated and continuous temperature monitoring provides a significant increase in the amount of data available for analysis of the patient's health. Hereinafter, "continuous" temperature monitoring refers to automated collection of temperature data at intervals, preferably regular intervals but irregular intervals are also contemplated.

Based on the greatly increased amount of temperature data collection with such monitors, it has been found that the fever associated with CRS has certain distinguishing characteristics that may be used for identification/diagnosis of CRS and/or the onset of fever, generally. In other words, CRS temperature and fever profiles (e.g., those shown and discussed below) are distinct from other known temperature and fever profiles caused by other known disease conditions and/or treatments, such as those from a transplant patient that has not received CAR-T therapy and is therefore is not experiencing a CRS event or those from a cancer patient receiving chemotherapy and experiencing a febrile neutropenia event. Accordingly, CRS fevers (and fevers associated with other causes) have profiles that can be identified (thus identifying CRS or the other cause) by analyzing temperature data collected by the above-described temperature monitors.

These characteristics may be identified by analysis of the temperature data collected by a temperature model. Such analysis can include any analysis of the temperature profile including, for example, the duration, rate of change, magnitude (e.g., maximum temperature), periodicity, and the like. Further, machine learning systems can be trained with temperature profiles and risk factor profiles to identify and diagnose particular types of fevers and diseases.

For example, the identification/diagnosis of CRS by way of temperature data can be based, at least in part, upon temperature data that is accumulated over a particular time period with the above-noted continuous temperature monitors. Such data may be processed automatically by computer analysis, or assembled into a graphical format for visual analysis by a clinician, as at least one basis for identifying key indicators for a CRS condition. Conveniently, the graphical format can readily be viewed and understood by doctors, nurses, or other hospital staff for confirmation of the automated computer analysis.

An example temperature profile for a CAR-T patient experiencing a typical CRS response is illustrated in FIG. 1. Four distinct fevers (F1-F4) above a 38° C. temperature threshold can be identified therein. Low temperatures (e.g., those below a 34° C. threshold) correspond to noise readings, for example, when the continuous temperature monitor is removed or replaced. The individual fever (F1-F4) profiles from the temperature profile of FIG. 1 are each illustrated in FIGS. 2 and 3.

Figure 2:
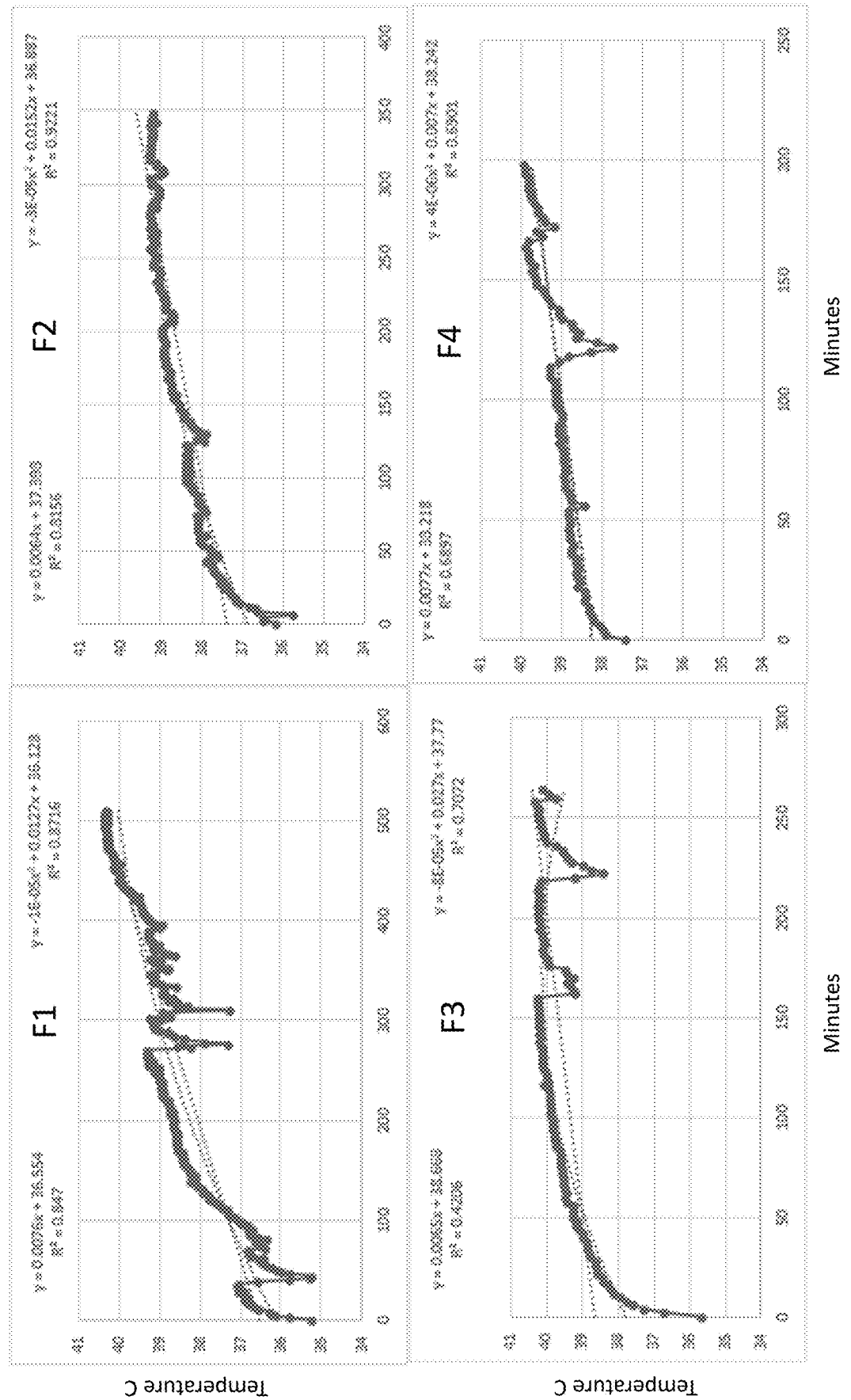
FIG. 2 illustrates each fever profile of FIG. 1 separately, overlaid with the results of two regression analyses.
Figure 3:
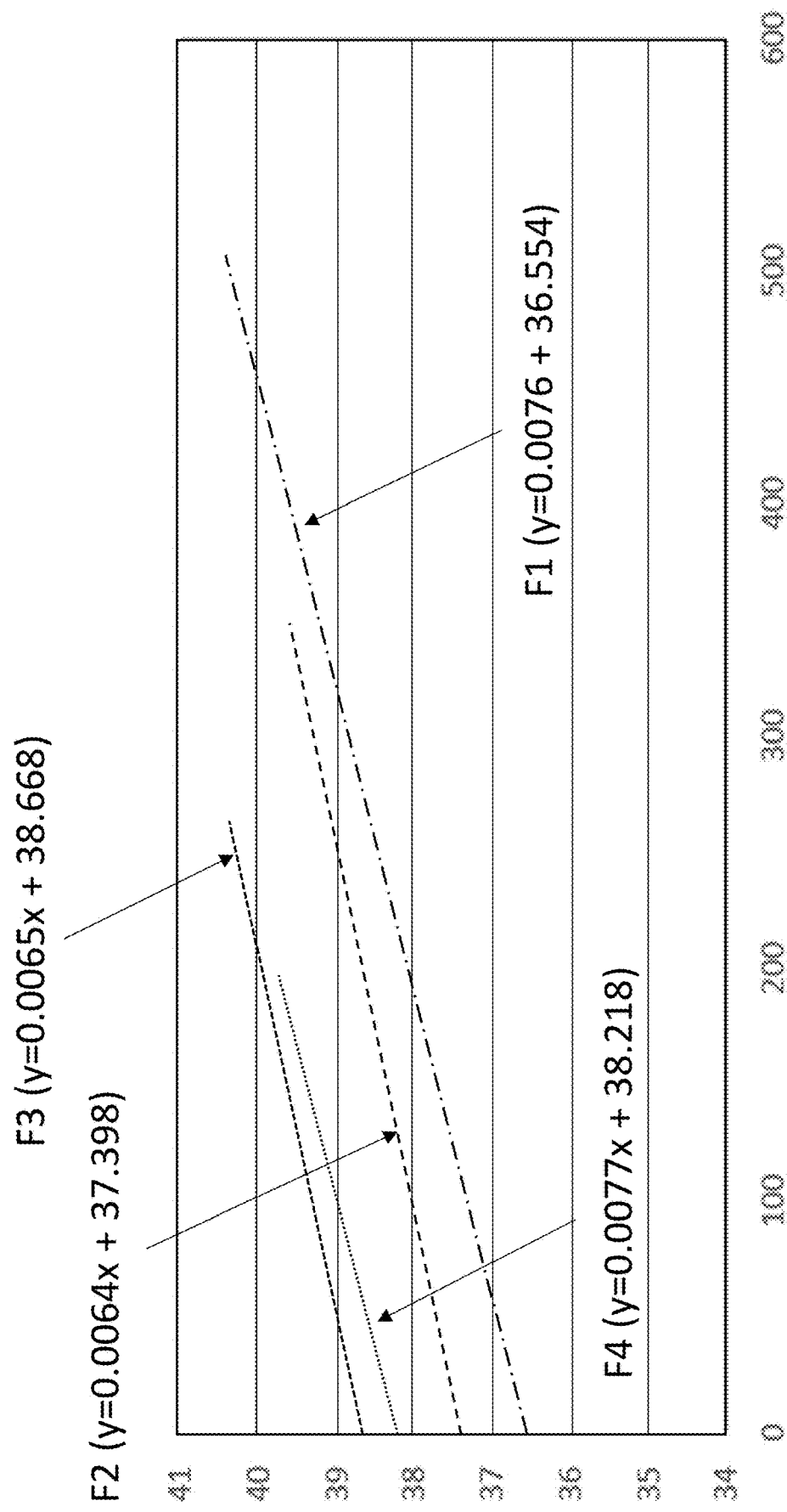
FIG. 3 comparatively illustrates the linear regression results for each fever profile of FIG. 1 on a common timeline.
Figure 4:
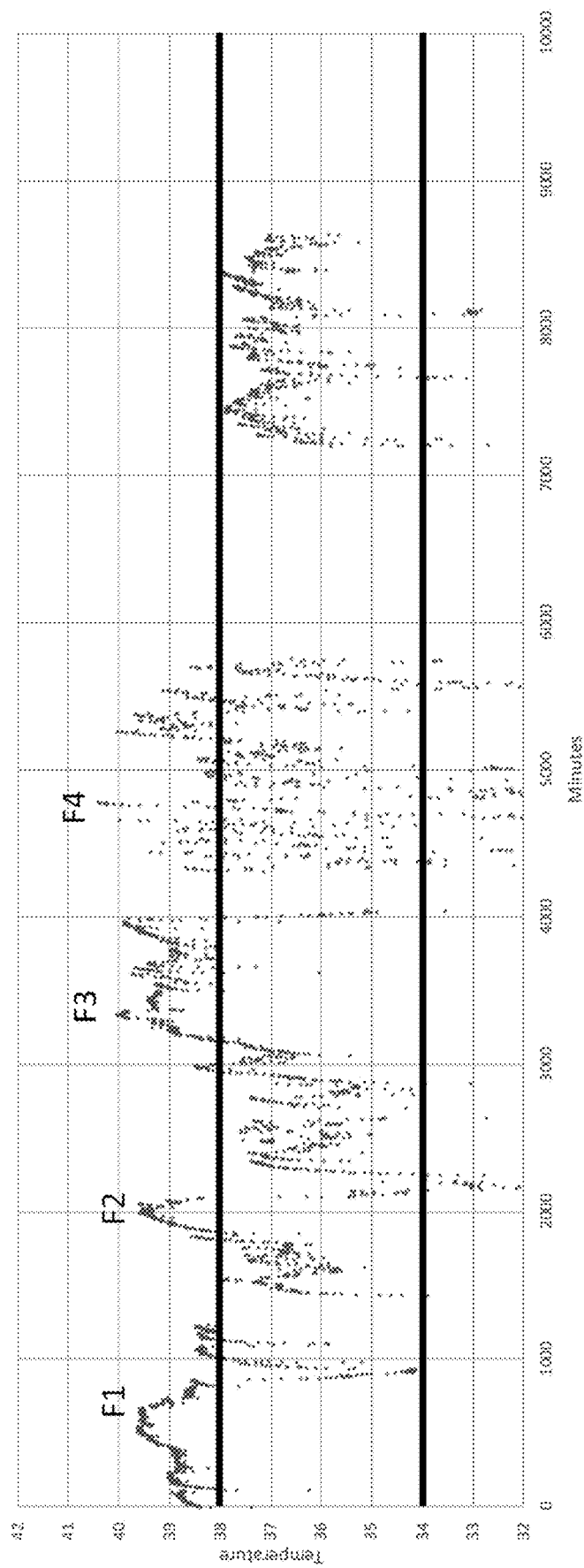
FIG. 4 illustrates an example CRS temperature profile from a second CAR-T patient.
Figure 5:
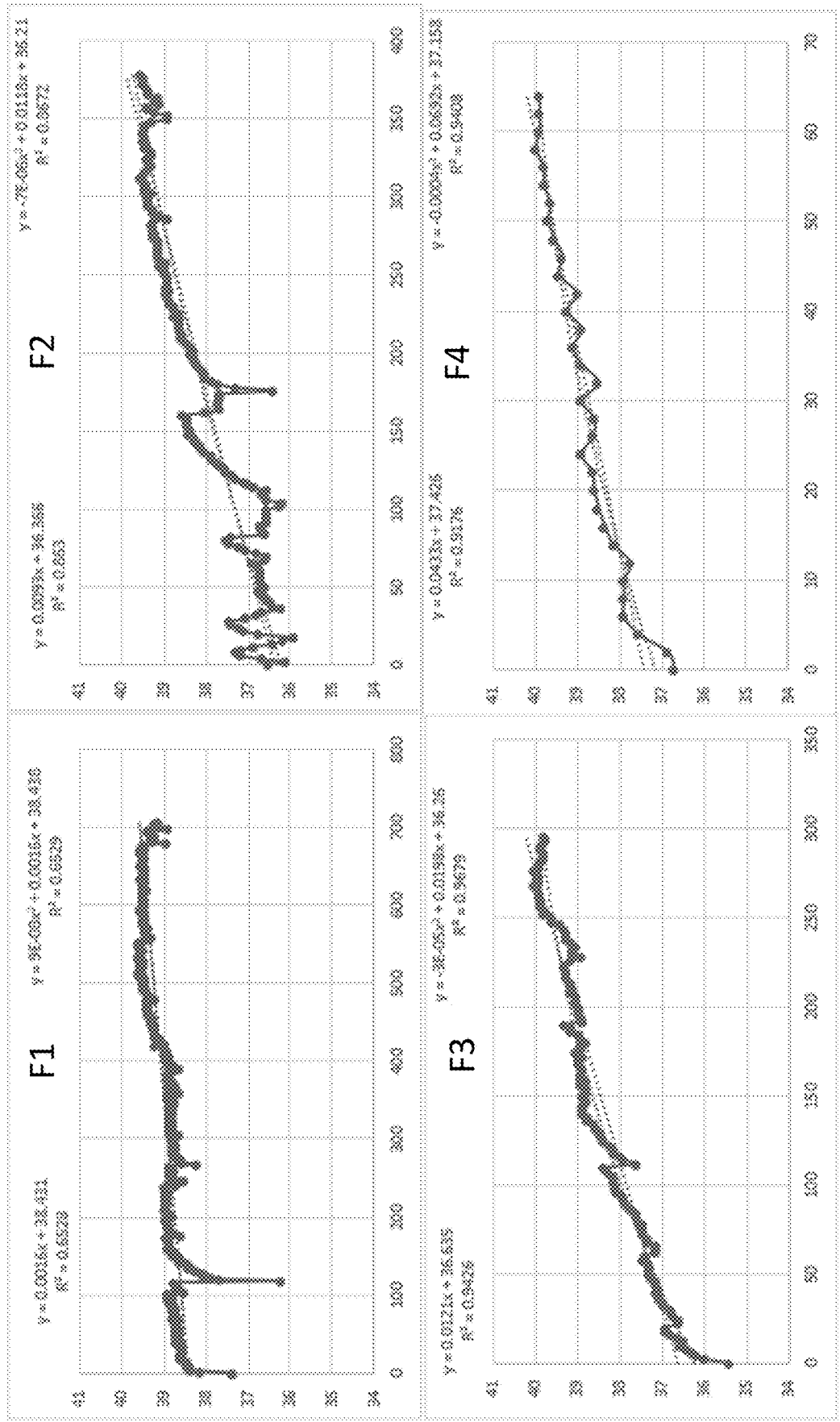
FIG. 5 illustrates each fever profile of FIG. 4 separately, overlaid with the results of two regression analyses.
Figure 6:
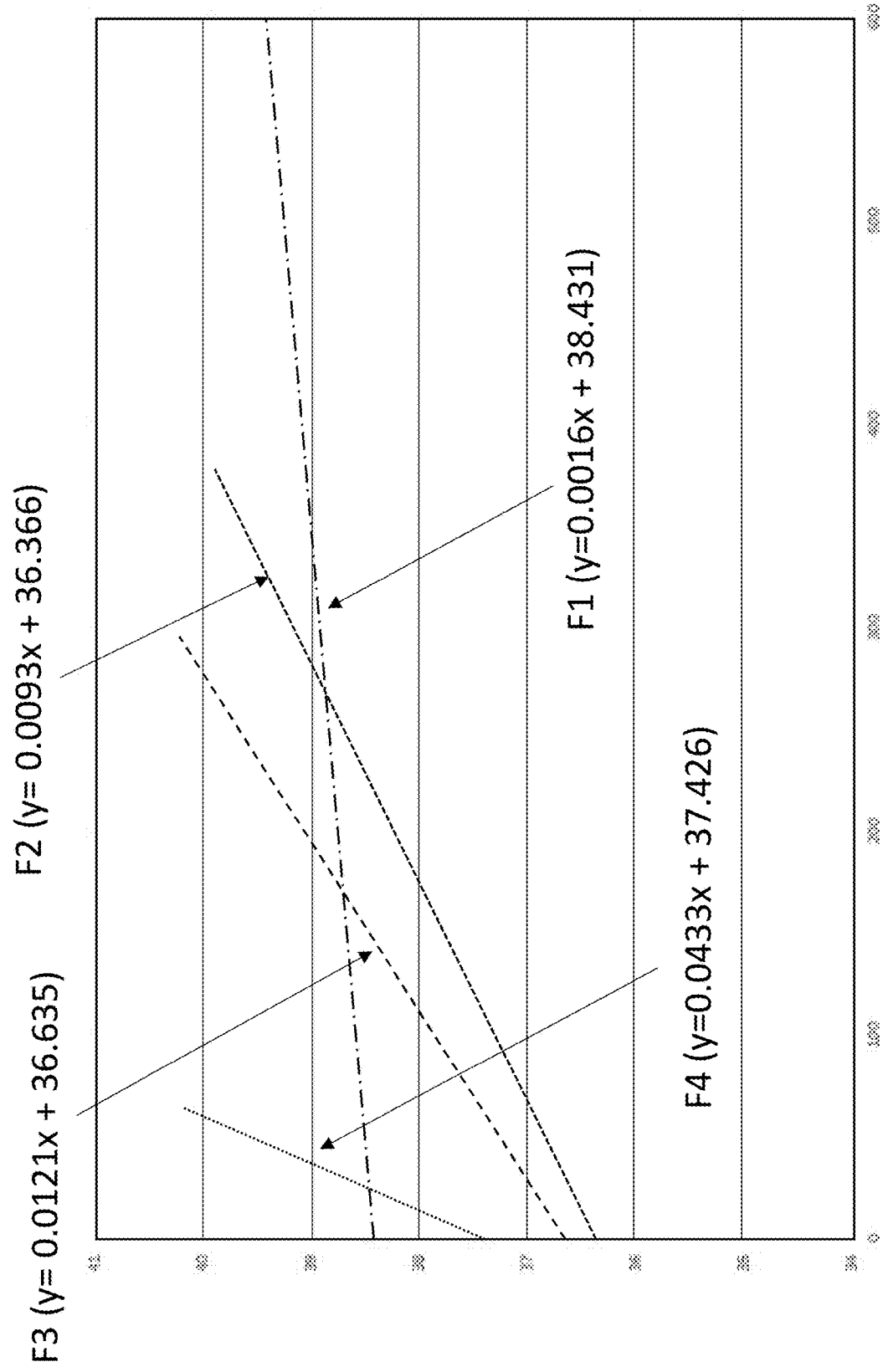
FIG. 6 comparatively illustrates the linear regression results for each fever profile of FIG. 4 on a common timeline.

Therein, the fever profiles F1-F4 are shown for the time period during which the temperature rises, as the decrease in temperature may be the result of a treatment. FIG. 2 shows each fever profile separately, overlaid with the results of two regression analyses: a linear regression and a second order polynomial regression. It is noted that any other quantitative or qualitative analysis may be utilized including, for example, other regressions, models, and/or machine learning systems, to identify distinguishing characteristics of a temperature profile from continuous temperature monitoring data. The respective $R^2$ factors and resulting equations for each regression analysis are also indicated in the figure. It was found from these analyses that the second order polynomial regression had a slightly better coefficient of correlation, although it is believed that the linear regression can produce a sufficient result with a simpler analysis and resulting equation. FIG. 3 illustrates these linear regression for each fever profile. Similar temperature and fever profiles for a second example patient are illustrated in FIGS. 4, 5, and 6.

Collectively the above CRS temperature and fever profiles of FIGS. 1-6, and further for two additional patients, are summarized below in Table 2.

TABLE 2

Summary of CRS Fever Profiles

| | | FIGS. 1-3 | FIGS. 4-7 | Patient #3 | Patient #4 | Average |
|---|---|---|---|---|---|---|
| Fever One | Duration (mins) | 508 | 600 | 866 | 624 | 650 |
| | Duration (hrs) | 8.5 | 10.0 | 14.4 | 10.4 | 10.8 |
| | Slope | 0.0076 | 0.0016 | 0.0021 | 0.0035 | 0.0037 |
| | ° C. / Hr | 0.46 | 0.10 | 0.13 | 0.21 | 0.22 |

TABLE 2-continued

Summary of CRS Fever Profiles

|  |  | FIGS. 1-3 | FIGS. 4-7 | Patient #3 | Patient #4 | Average |
|---|---|---|---|---|---|---|
|  | ° F. / Hr | 0.82 | 0.17 | 0.23 | 0.38 | 0.40 |
| Fever Two | Duration (mins) | 342 | 376 | 212 | 256 | 297 |
|  | Duration (hrs) | 5.7 | 6.3 | 3.5 | 4.3 | 4.9 |
|  | Slope | 0.0064 | 0.0093 | 0.0099 | 0.0062 | 0.0080 |
|  | ° C. / Hr | 0.46 | 0.56 | 0.59 | 0.37 | 0.50 |
|  | ° F. / Hr | 0.83 | 1.00 | 1.07 | 0.67 | 0.89 |
| Fever Three | Duration (mins) | 260 | 296 | 352 | 422 | 333 |
|  | Duration (hrs) | 4.3 | 4.9 | 5.9 | 7.0 | 5.5 |
|  | Slope | 0.0065 | 0.0121 | 0.0206 | 0.0079 | 0.0093 |
|  | ° C. / Hr | 0.39 | 0.73 | 0.64 | 0.47 | 0.56 |
|  | ° F. / Hr | 0.70 | 1.31 | 1.14 | 0.85 | 1.00 |
| Fever Four | Duration (mins) | 200 | 64 | 212 |  | 125 |
|  | Duration (hrs) | 3.3 | 1.1 | 1.9 |  | 2.1 |
|  | Slope | 0.0077 | 0.0433 | 0.053 |  | 0.0347 |
|  | ° C. / Hr | 0.46 | 2.60 | 3.18 |  | 2.08 |
|  | ° F. / Hr | 0.83 | 4.68 | 5.72 |  | 3.74 |

In summary, CRS is characterized by a series of fevers. The initial fever (of three or four total) has the longest duration (about 9-10 hours) and the lowest rate of temperature increase (about 0.22° C./hr or 0.40° F./hr). The second and third fevers have about half the duration (about 5 hours) but about twice the rate of temperature increase during onset (about 0.5° C./hr or 1.0° F./hr), and represent the most common fever profile for CRS patients. The final fever is generally the most severe but for the shortest time (about 2 hours) with the quickest onset (about 1-2° C./hr or 3-4° F./hr). The indicated slope for each fever corresponds to the slope derived by the linear regression analysis.

Considering this, traditional temperature measurements occurring only once every two to four hours per the current standard of care are insufficient to provide the desired level of care. This is because such measurements may not detect the fever onset until it has spiked, or may miss the fever event entirely. However, continuous temperature monitoring as discussed above, and analysis of the above factors, can be utilized to recognize such temperature and fever profiles.

The identification/diagnosis of CRS and/or the fever may be further characterized by additional risk factors including, but not limited to, high disease burden (in acute lymphoblastic leukemia), high infusional dose, fludarabine containing lymphodepletion, concurrent infectious illness, early cytokine elevations. Still further, other criteria may indicate CRS, including any or all of the following: that the patient was treated with CAR-T therapy within the last days/weeks; that the patient is at an elevated risk for CRS fever; that the patient is currently at a lower risk for other diseases.

Accordingly, the above-noted and other recognized characteristic features of CRS fevers, can be compared to recorded temperature data during continuous temperature monitoring as a real-time (or near real-time) analysis to identify the onset or existence of CRS. The additionally described risk factors for CRS can also be considered as part of the analysis. A diagnosis of CRS, or likelihood of CRS, can thus be output to a clinician or patient as a result of this analysis. In other words, analysis of a fever profile collected by a continuous temperature monitor, associated risk factors, and additional criteria present in a patient can be utilized to identify a CRS fever (and thus diagnose CRS), and/or identify a confidence level of such an identification and/or diagnosis. Additionally, such information may be used to predict (e.g., at a particular confidence level) the onset of CRS prior to the patient actually expressing a fever.

As suggested above, rather than using a regression, the analyses and determinations of temperature data may be performed by a machine learning system. For example, the machine learning system may include a Multi-step Multi-layer Perceptron (MLP) network. An MLP is a type of feedforward neural network, which is robust to noisy input data and capable of learning linear and nonlinear relationships in training data. Further, because MLPs can provide multiple outputs, the MLP can produce a forecast for multiple future time points. However, because MLPs have a fixed input and output, the MLP has a pre-determined temporal dependence. In other words, the time periods of input and output temperature data (the number of input and output points) is pre-determined.

In one embodiment of an MLP network, the temporal dependence is a three hour input (a collection time period) and a one hour output (a future time period). For a temperature monitor having a frequency of one measurement every six minutes, this corresponds to thirty input points (30 time point inputs×6 minute intervals=180 minutes=3 hours) and ten output points (10 time point outputs×6 minute intervals=60 minutes=1 hour). In other words, given a prior three hours of data, the MLP is trained to predict the following hour of temperature data. It is understood that other input and output time periods are within the scope of the present disclosure. For example, in other embodiments, the number of input and output data points may vary, for example, between 5 and 60.

According to one embodiment, the MLP has a single hidden layer of 200 units using a rectified linear unit activation function, and an input dimension of thirty time steps (or other time step that corresponds to a desired input time period for a given collection frequency). In other embodiments, the number of units of the hidden layer may be, for example, 50-2000. Further, more than one hidden layer may be included. The hidden layer(s) is followed by an output layer with an output dimension of ten time steps (or other time step that corresponds to a desired output time period for a given collection frequency). The MLP is fit, for 250 epochs, using stochastic gradient descent with the Adam optimization algorithm, and uses mean squared error as the loss function. In other embodiments, the MLP may have 50-2000 epochs. Predictions are made by then passing in thirty consecutive data points (or appropriate number of data points corresponding to a desired input time period for a given collection frequency), and the output is the predicted ten following data points (or appropriate number of data points corresponding to a desired output time period for a given collection frequency).

Temperature data collected by the continuous temperature monitors is pre-processed to remove all data points having a temperature at or below a predetermined threshold (e.g., 34° C., or 0° C.). This is because such low readings can be considered improper, for example, as the result of the monitor being improperly attached to the patient, removed, or the like. The data having low temperatures removed is then assembled in a sequence array. Further, because temperature data from a single patient may be collected from more than one temperature monitor, the data is combined into a single array, arranged temporally. Removed data points (those below a predetermined threshold) and/or missing data points from times when no temperature data is collected (e.g., times between monitor uses) can be treated as NULL, estimated via statistical techniques such as interpolation, or otherwise corrected. The MLP is trained with existing temperature data from known CAR-T patients. As additional data is collected from more patients, establishing a larger collection of historical data identifying ground truth temperature and fever profiles, the MLP may be further trained with that data.

Figure 7:
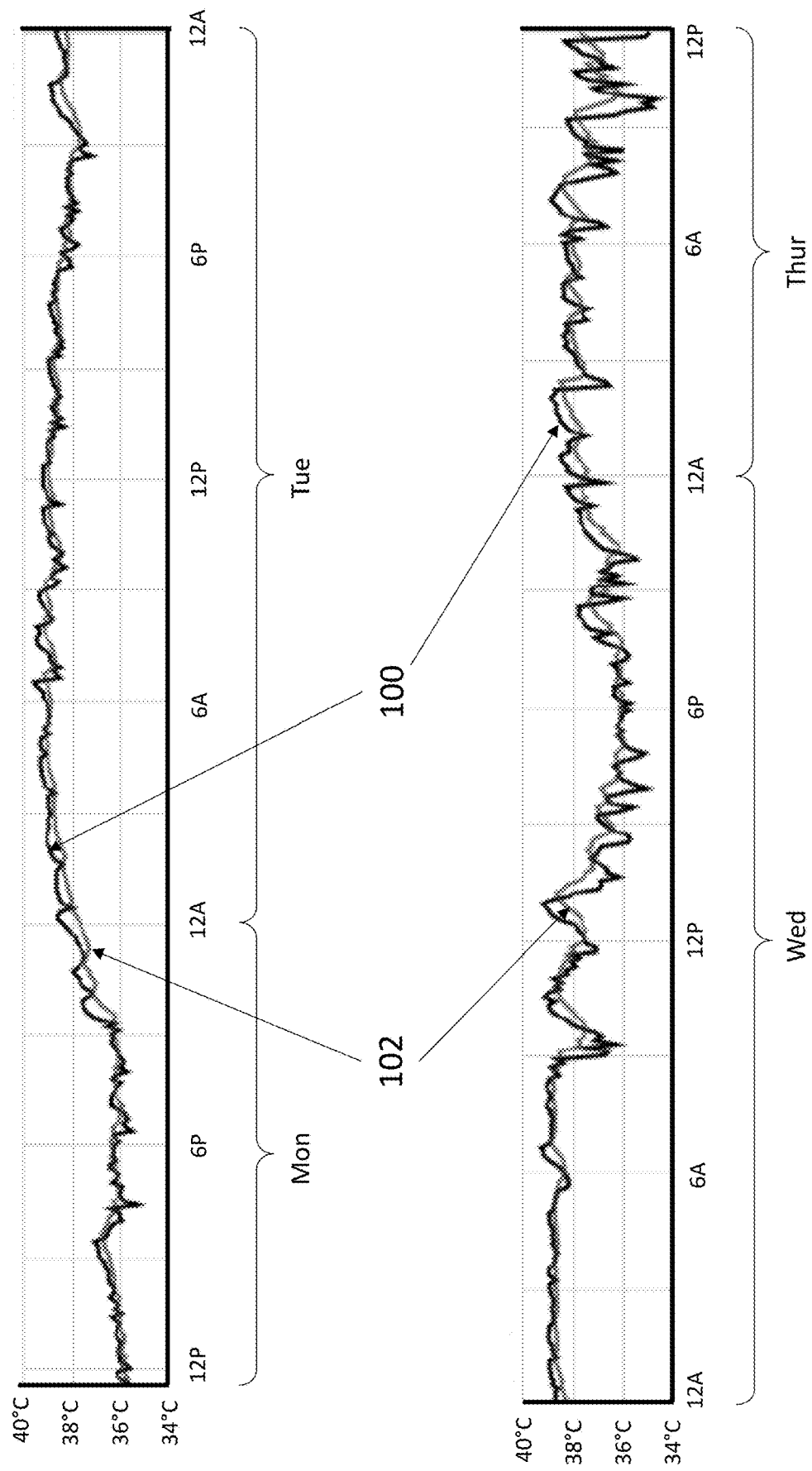
FIG. 7 illustrates example temperature prediction results from a machine learning system.

An example output of such a machine learning system is illustrated in FIG. 7. Therein, an MLP was trained with temperature data from thirteen patients having a combined total of 58 thousand rows of non-zero temperature data. The graph of FIG. 7 illustrates recorded non-zero temperature data 100 (dark black line) for one patient, with readings beginning on Monday at 12 pm and ending Thursday at 12 pm, and the corresponding predicted temperature 102 output by the MLP. As can be seen, the predicted temperature profile 102 (light gray line) closely follows the actually recorded temperature data 100 representing the ground truth.

In still other examples, the machine learning system may include Convolutional Neural Networks (CNNs) including Univariate Multi-step CNNs and Temporal Convolutional Networks (TCNs), Long-Short-Term Memory (LTSM) models (which can learn the temporal dependence), and/or Sequence to Sequence (S2S) models. Such systems may be trained with training data similar to that discussed above with respect to an MLPs.

Figure 8:
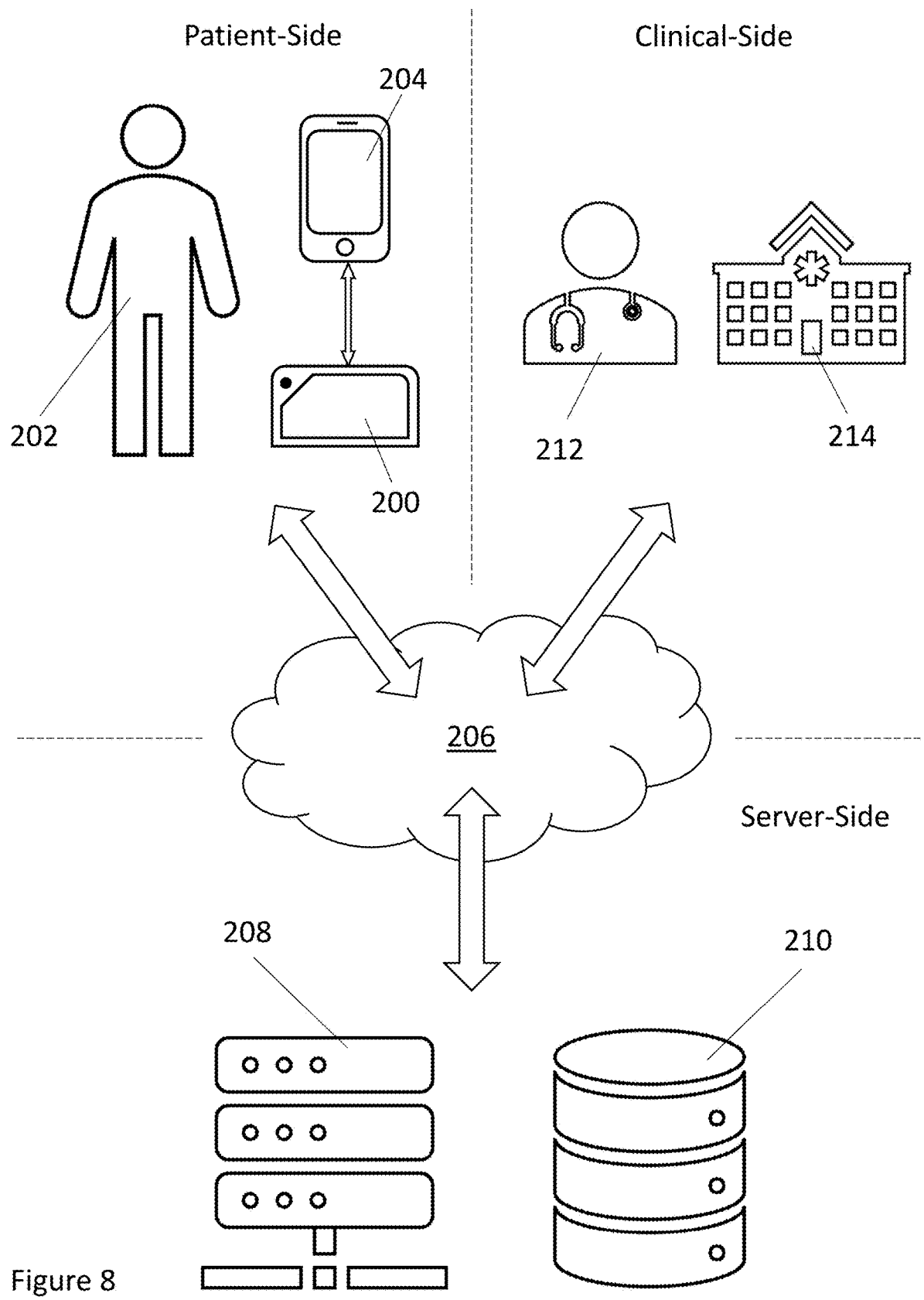
FIG. 8 illustrates an example system for temperature prediction and monitoring.
Figure 9:
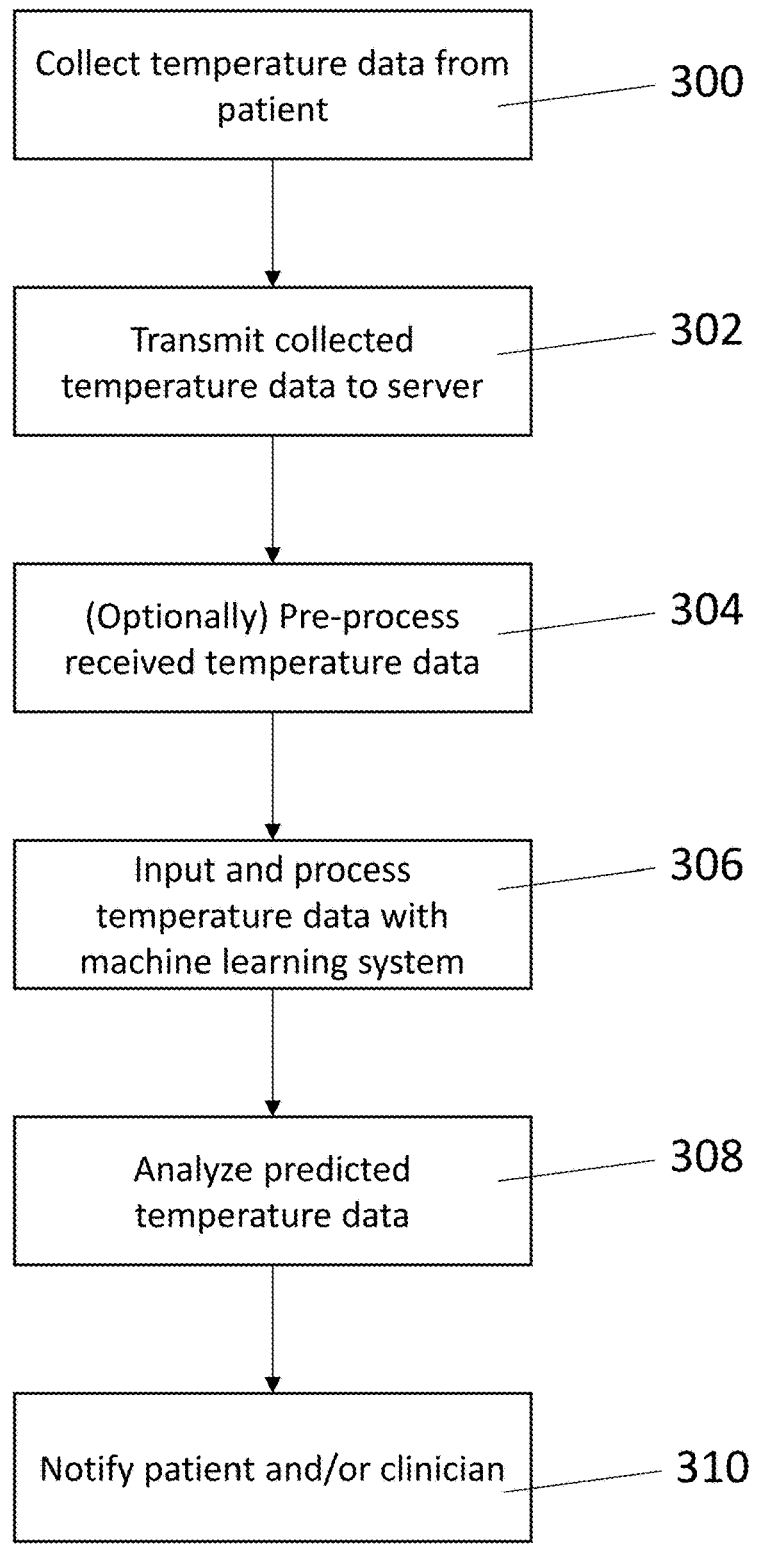
FIG. 9 illustrates an example method for temperature prediction and monitoring.

With reference to FIGS. 8 and 9, in use, temperature data is collected 300 at a patient-side from a continuous temperature monitor 200 on a patient 202. The patient 202 may monitor the collected temperature data in real-time, along with previously detected temperature data, trends, and the like, on a personal device 204 (e.g., cell phone, computer, or the like). The personal device 204 may communicate with the monitor 200 via any short range communication including, for example, Bluetooth, near field communication, and the like.

The collected temperature data is then transmitted 302 over a network (e.g., the Internet) 206 to a server-side computer system 208. The computer system 208 comprises a processor, database/memory, and the like. The computer is configured at least in part as a machine learning system, such as the above-discussed MLP, and/or is otherwise configured to perform analysis on the received temperature data. The database/memory is configured to store temperature data received from the monitor 200, and the processor is configured to pre-process 304 the received temperature data as described above, and process the collected/stored temperature data 306 from the monitor 200 with the machine learning system. In other embodiments, the temperature data may be stored at a remote database 210 from the machine learning system/computer 208. In other embodiments, the computer system 208 including any data processing and/or analysis may additionally or alternatively be implemented in part or in whole locally at the patient-side, for example, on the patient's personal device 204.

In one form, after optionally being subject to the above-described pre-processing 304, the received temperature data may be compared to a threshold temperature to determine whether the patient 202 is currently experiencing (or had previously experienced) a fever. In the event the patient 202 has a fever, the computer system 208 may transmit an alert to the patient's personal device 204 at the patient-side and/or a doctor 212, hospital 214, or like clinician at a clinical-side, via network 206. These alerts may further include instructions to the patient to, for example, seek medical attention. The output may also include the received temperatures and/or a temperature profile for review and analysis by the doctor 212 at the clinical-side.

After enough temperature data has been collected to satisfy the temporal dependence (e.g., three hours of temperature data) of the machine learning system, the received temperature data is input to the machine learning system to be processed 306 by the machine learning system at the server-side. In one embodiment, the temperature data is input to the machine learning system as it is received from the patient-side. For example, according to the above description, temperature data may be received and input every six minutes, corresponding to the frequency of temperature data collection by the monitor 200. In other embodiments, the data may be input to the machine learning system at other intervals (e.g., every hour) with the most recently collected temperature data.

The output of the machine learning system of the computer system 208 is predicted temperature data (a predicted temperature profile) for a period of time corresponding to temporal dependence of the system (e.g., one hour of temperature data). The outputted prediction data may be further analyzed 308 by the computer system 208 to take a form suitable for review by a doctor 212 or patient 202, and then transmitted as a notification 310 through the network 206 to the doctor 212, hospital 214, or the like at a clinical-side, and/or to the patient's personal device 204 at the patient-side.

For example, the predicted temperature profile may be output as the notification to the patient 202, doctor 212, and/or hospital 214 in the form of a time-series graph, or a narrative indicating the patient's current or predicted future condition. An alert may further be transmitted as part of the notification if a fever is predicted based on analysis of the output of the machine learning system.

The fever prediction may result from comparison of a future temperature to a fever threshold, an identification of rate of increase of temperature in the predicted data exceeding a predetermined threshold, a period of time of the temperature in the predicted data above a predetermined threshold, or the like. In some embodiments, the fever prediction based on the predicted temperature data may be based on an analysis of the predicted temperature profile to known fever, patient, and therapy characteristics, such as those discussed above and those provided in Table 2. In some embodiments a second machine learning system of the server-side computer system 208 is trained to classify the predicted temperature data as a potential fever onset. In such cases, the predicted temperature profile may be supplied to the second machine learning system, whose output is a determination that the predicted temperature profile does/does not correspond to a fever profile. In other words, the collected and/or predicted temperature data may be analyzed to determine a future onset of fever. Further, by identifying the existence or prediction of a fever, a diagnosis of CRS can be made and indicated in the notification.

The output may also instruct a user to perform a task (e.g., seek medical treatment) based on the predicted temperature profile, indicate an average temperature over a period of time (past or future), indicate any recent or predicted trends in temperature (e.g., rate of temperature increase or decrease), indicate a period of time (past or future) the temperature data is above a predetermined threshold temperature, and the like. Still further, alerts related to any errors in receiving temperature data from the monitor 200, or the occurrence of abnormal data (e.g., low temperature readings), can be transmitted to the patient-side and/or clinical-side. Accordingly, the patient 202 may be made aware of operation, connection, or like problems with the monitor 200, and how those problems may be corrected.

Any of the outputs described herein may be provided in as close to real time as practically possible. That is, the computer system 208 may be configured to process any temperature data 306 upon receipt, and conduct any subsequent analysis and produce any of the desired outputs upon the determination of the prediction temperature data (e.g., from the machine learning system). For example, as suggested above, temperature data may be transmitted 302 to the computer system 208 from the monitor 200 at intervals corresponding to the frequency of temperature collection by the monitor 200. By processing this received temperature data upon receipt, the patient 202, doctor 212, and/or hospital 214 may be notified by the output (e.g., an updated predicted temperature profile or fever alert) at substantially the same frequency. In this manner, the patient and clinicians may be kept aware of the patient's condition in real time as the temperature data is collected.

Although the above description relates primarily to CRS and CAR-T, the scope of the present disclosure is not so limited and may relate to different temperature profiles and risk factors associated with other conditions and diseases. For example, these other conditions and diseases may include autoimmune diseases, such as rheumatoid arthritis, Crohn's disease/colitis, lupus, Behcet syndrome, blood clots, deep vein thrombosis, and pulmonary embolisms; neurological disorders such as spinal cord injury and stimulant overdoses; psychological disorders; neoplasms such as lymphoma, leukemia, and hypernephromas; endocrine disorders such as hyperthyroidism and adrenal insufficiency; and transfusion reactions. Therefore, similar continuous temperature monitoring and analysis of the resulting temperature data and corresponding risk factors can also be used for diagnosis of those conditions.

What is claimed is:

1. A method comprising:
   receiving temperature data from a continuous temperature monitor worn by a patient, the continuous temperature monitor comprising a flexible patch configured to be attached to the patient's skin, the flexible patch comprising a temperature sensor that is configured to automatically collect at least one temperature of the patient every five minutes during a collection time period;
   inputting the received temperature data to a machine learning system, the machine learning system being trained to output a predictive temperature profile of the patient based upon the received temperature data, the predictive temperature profile comprising predicted temperature values of the patient at a plurality of corresponding times in a future time period;
   analyzing the predictive temperature profile for an indication of a fever during at least one of the plurality of times in the future time period; and
   transmitting a notification of a result of the analysis to a personal device of the patient and/or to a clinician,
   wherein the notification comprises an alert when the result of the analysis indicates the fever, and
   wherein the notification is transmitted in substantially real time with the receipt of the temperature data and result of the analysis.

2. The method of claim 1, wherein the flexible patch comprises a wireless transmitter, and wherein the machine learning system is remotely connected to the continuous temperature monitor and to the clinician via a network.

3. The method of claim 1, wherein the machine learning system is trained with temperature data from subjects having a same medical condition as the patient.

4. The method of claim 3, wherein the same medical condition is cytokine release syndrome.

5. The method of claim 1, further comprising correcting received temperature data points having a value below a predetermined threshold prior to inputting the received temperature data to the machine learning system.

6. The method of claim 1, wherein analyzing the predictive temperature profile for the fever comprises comparing the predicted temperature values to a predetermined threshold.

7. The method of claim 1, wherein analyzing the predictive temperature profile for the fever comprises comparing a rate of increase of the predictive temperature profile to a predetermined threshold.

8. The method of claim 1, wherein the collection time period is three hours long and the future time period is one hour long.

9. The method of claim 1, wherein the notification further comprises an instruction to the patient to seek medical attention when the result of the analysis indicates the fever.

10. The method of claim 1, wherein the machine learning system comprises a multi-step multi-layer perceptron network.

11. The method of claim 1, wherein the machine learning system comprises a univariate multi-step convolutional neural network.

12. The method of claim 1, wherein the machine learning system comprises a long-short-term memory model.

13. The method of claim 1, wherein the machine learning system comprises a sequence to sequence model.

14. The method of claim 1, further comprising:
    when the result of the analysis indicates the fever, treating the medical condition of the patient prior to the corresponding time in the future time period at which the fever is predicted to occur.

15. The method of claim 1, wherein analyzing the predictive temperature profile for the fever comprises determining a period of time the predictive temperature profile is greater than a predetermined threshold temperature.

16. The method of claim 1, wherein the patient is undergoing or has undergone chimeric antigen receptor T-cell (CAR-T) therapy, and the fever is caused by cytokine release syndrome.

17. The method of claim 1, wherein the notification further comprises a time series graph of the predicted temperature values at the plurality of corresponding times in the future time period.

18. The method of claim 1, wherein the collection time period is thirty minutes long and the future time period is one hour long.

\* \* \* \* \*